(12) United States Patent
Schmidt et al.

(10) Patent No.: US 7,094,531 B1
(45) Date of Patent: Aug. 22, 2006

(54) NUCLEIC ACID SEQUENCING

(75) Inventors: Gunter Schmidt, Houghton (GB);
Andrew Hugin Thompson, Alloway (GB)

(73) Assignee: Xzillion GmbH Co. (DE)

( * ) Notice: Subject to any disclaimer, the term of this patent is extended or adjusted under 35 U.S.C. 154(b) by 0 days.

(21) Appl. No.: 09/341,641

(22) PCT Filed: Jan. 15, 1998

(86) PCT No.: PCT/GB98/00130

§ 371 (c)(1),
(2), (4) Date: Sep. 9, 1999

(87) PCT Pub. No.: WO98/31831

PCT Pub. Date: Jul. 23, 1998

(30) Foreign Application Priority Data

Jan. 15, 1997 (GB) .......................................... 9700760.3

(51) Int. Cl.
*C12Q 1/68* (2006.01)
*C12N 15/00* (2006.01)
*C12N 15/63* (2006.01)
*C12N 1/20* (2006.01)
*C07H 21/04* (2006.01)

(52) U.S. Cl. ...................... 435/6; 435/320.1; 435/252.8; 435/174; 435/183; 382/129; 382/133; 382/153; 382/173; 382/286; 382/291; 702/19; 702/22; 935/10; 935/24; 935/72; 536/22.1

(58) Field of Classification Search ...................... 435/6, 435/91.1, 91.2, 320.1; 536/24.3, 23.4, 22.1, 536/24.33; 935/6; 436/518; 530/350
See application file for complete search history.

(56) References Cited

U.S. PATENT DOCUMENTS

| 5,124,247 A | | 6/1992 | Ansorge | |
|---|---|---|---|---|
| 5,503,980 A | * | 4/1996 | Cantor | ........................... 435/6 |
| 5,866,328 A | * | 2/1999 | Bensimon et al. | .............. 435/6 |

FOREIGN PATENT DOCUMENTS

| WO | WO 95/04160 | * | 2/1995 | .................... 435/6 |
|---|---|---|---|---|
| WO | WO 95/09248 | | 4/1995 | |
| WO | WO 95/20053 | | 7/1995 | |
| WO | WO 96/33205 | * | 10/1996 | .................... 435/6 |

OTHER PUBLICATIONS

*Stratagene Catalog*, p. 39, 1988.*
Stratagene Catalog, p. 39, 1988.*

* cited by examiner

*Primary Examiner*—B J Forman
(74) *Attorney, Agent, or Firm*—Buchanan Ingersoll PC

(57) ABSTRACT

Provided is a method for sequencing DNA, which comprises: (a) obtaining a target DNA population comprising one or more single-stranded DNAs to be sequenced, each of which is present in a unique amount and bears a primer to provide a double-stranded portion of the DNA for ligation thereto; (b) contacting the DNA population with an array of hybridisation probes, each probe comprising a label cleavably attached to a known base sequence of predetermined length, the array containing all possible base sequences of that predetermined length; (c) removing all unligated probes; followed by the steps of: (d) cleaving the ligated probes to release each label; (e) recording the quantity of each label; and (f) activating the extended double-stranded portion to enable ligation thereto; wherein (g) steps (b) to (f) are repeated in a cycle for a sufficient number of times to determine the sequence of the or each single-stranded DNA by determining the sequence of release of each label.

11 Claims, 8 Drawing Sheets

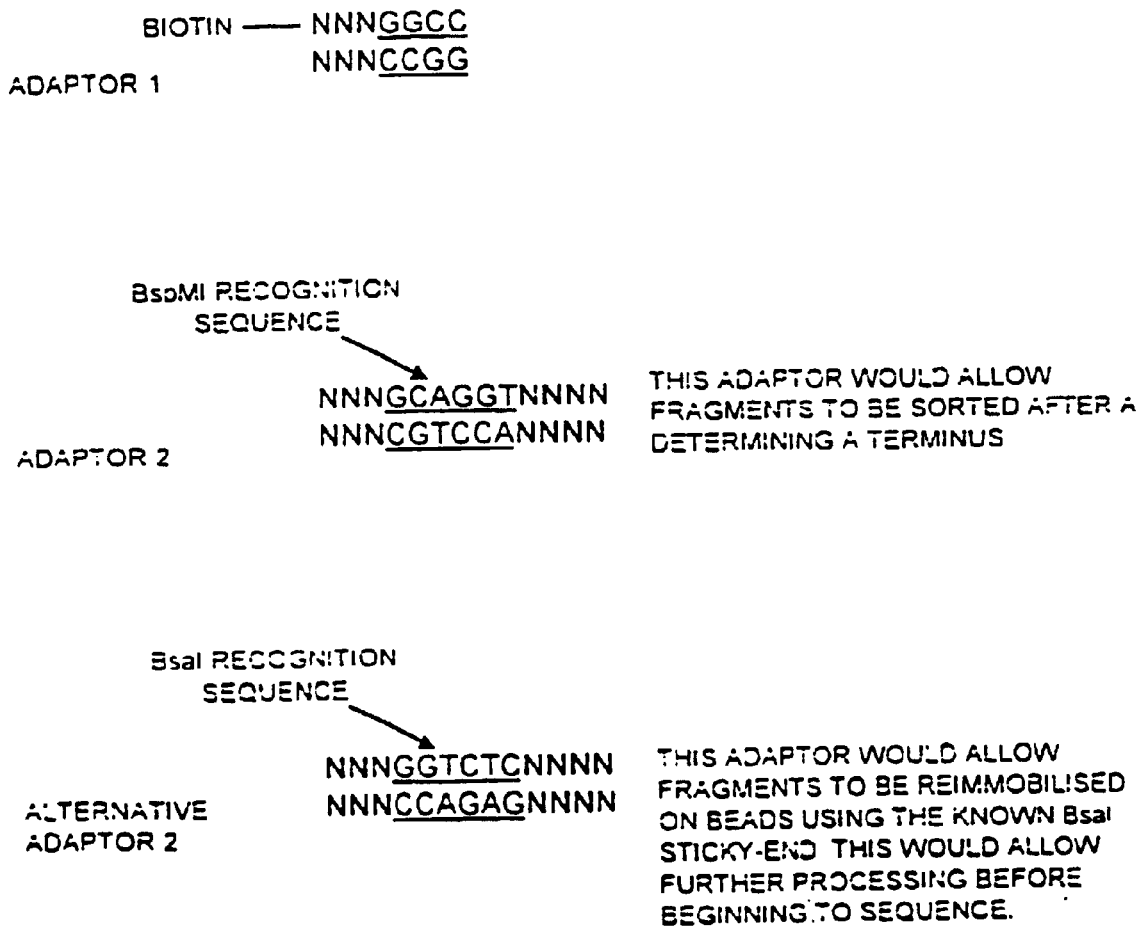
FIG. 3 ADAPTORS TO GENERATE DISTINCT TERMINI IN GENERIC NUCLEIC ACIDS.

DIAGRAM TO SHOW PREPARATION OF SINGLE-STRANDED DNA FOR PRIMER EXTENSION SEQUENCING.

NUCLEIC ACID SEQUENCING

The present invention relates to a method for sequencing DNA and a kit for sequencing DNA.

Traditional methods for sequencing nucleic acid such as DNA frequently require biological sub-cloning hosts and vectors. Such traditional methods generally require gel chromatography to acquire sequence information. These, traditional methods are therefore often complicated multi-stage processes which are both time-consuming and labour intensive.

PCT/US96/05245 discloses a method of nucleic acid sequencing based on an iterative process of duplex extension along a single-stranded template. Duplex extension is effected by ligating probes to a region of the template primed with an initialising oligonucleotide. The probes of the above method are labelled preferably with a fluorescent dye. The dye identifies a single base at the ligation site. The probes are prevented from uncontrolled extension by having removable blocking groups at one of their terminals.

PCT/US95/00109 suggests a method of nucleic acid sequencing comprising sequentially extending a primer a pre-determined number of bases at a time, the added bases being complementary to the bases being sequenced. This is achieved by contacting the nucleic acid with a labelled adaptor, the label being specific to the base sequence of the adaptor. A population of adaptors is used having oligonucleotide sequences including all possible permutations for a pre-determined number of bases.

The present invention provides a method for sequencing DNA, which comprises:

(a) obtaining a target DNA population comprising one or more single-stranded DNAs to be sequenced, each of which is present in a unique amount and bears a primer to provide a double-stranded portion of the DNA for ligation thereto;

(b) contacting the DNA population with an array of hybridisation probes, each probe comprising a label cleavably attached to a known base sequence of predetermined length, the array containing all possible base sequences of that predetermined length and the base sequences being incapable of ligation to each other, wherein the contacting is carried out in the presence of ligase under conditions to ligate to the double-stranded portion of each DNA the probe bearing the base sequence complementary to the single-stranded DNA adjacent the double-stranded portion thereby to form an extended double-stranded portion which is incapable of ligation to further probes; and (c) removing all unligated probes; followed by the steps of:

(d) cleaving the ligated probes to release each label;

(e) recording the quantity of each label; and (f) activating the extended double-stranded portion to enable ligation thereto; wherein (g) steps (b) to (f) are repeated in a cycle for a sufficient number of times to determine the sequence of the or each single-stranded DNA by determining the sequence of release of each label.

In one embodiment the array comprises a plurality of sub-arrays which together contain all the possible base sequences, and wherein each sub-array is contacted with the DNA population according to step (b), unligated probes are removed according to step (c), and these steps are repeated in a cycle before step (d) so that all of the sub-arrays contact the DNA population. In this way, the array of hybridisation probes is presented to the DNA population in stages. For example, where the predetermined length of base sequence is 4 and the total number of possible base sequences is 256 ($4^4$), cross-hybridisation between complementary 4-mer in the array can be avoided by contacting the DNA population with a first sub-array of 128 probes and, after removing all unligated probes, contacting with a second sub-array of 128 probes.

The target DNA population may be obtained by sorting an initial DNA sample into sub-populations and selecting one of the sub-populations as the target DNA population. Thus, if the initial DNA sample is large its size can be reduced by the sorting step. In a preferred arrangement, the initial DNA sample is cut into fragments, each having a sticky end of known length and unknown sequence, typically a length of from 2 to 6, preferably about 4 bases. The fragments may be sorted into sub-populations according to their sticky end sequence. It is thought that a population or sub-population of at least 60 fragments can be sequenced in parallel with an acceptable error rate using a probe with a base sequence of 4 bases.

Preferably, each single-stranded DNA is immobilised, usually at one end, for example on a solid support such as a bead. This has the advantage that removal of unwanted material can take place in solution and separation of the labels from the probes is facilitated. Preferably, the target DNA is immobilised prior to step (b) on the solid phase support. The solid phase support may conveniently be attached to the primer.

The label may be any suitable label such as a fluorescent label, a radio label or a mass label. The identity of the label must be assignable to the respective base sequence so that identification of the label identifies the base sequence. In a preferred arrangement, the label of each probe comprises a mass label. Each mass label is uniquely identifiable in relation to every other mass label using a mass spectrometer. Typically each mass label has a distinct mass from every other mass label and preferably a single ionization state at the pH of analysis in a mass spectrometer. Each mass label preferably does not fragment in the mass spectrometer. Preferred mass labels do not interfere with the action of the ligase in the sequencing method or with any other of the molecular biology steps used in the invention.

Where the label is a mass label, the quantity of each label corresponding to the ligated hybridisation probe is recorded in step (e) after release of the label in step (d). Where the label is a fluorescent label, step (e) may precede step (d) and the quantity of fluorescent label present on the ligated probe is recorded before the label is released.

In any one cycle of the method according to the invention it is essential that the base sequence of only one probe ligates to the double-stranded portion of each DNA. The base sequences of the probes of the array are therefore incapable of ligation to each other so that the extended double-stranded portion which is formed after ligation is incapable of ligation to further probes. In subsequent step (f), the extended double-stranded portion is activated to enable ligation thereto of a further probe in the next cycle. The base sequences may be incapable of ligation to each other either by requiring activation or by being blocked to prevent ligation thereto.

In one embodiment of the invention the known base sequence is blocked at its 3'OH. According to this embodiment, primer extension sequencing takes place in the 5' to 3' direction. In another embodiment of the invention, the base sequences are capable of ligating to each other only when activated by phosphorylation. According to this embodiment, the base sequence of each probe is unphosphorylated at both 3' and 5' ends and activation step (f) comprises phosphorylating the 5'-OH of the extended double-stranded portion to enable ligation thereto.

Advantageously, the step (d) of cleaving the ligated probes to release each label unblocks the 3'-OH of the extended double-stranded portion according to step (f). In other words, step (d) and step (f) are one and the same. Preferably, the label of each probe is cleavably attached to the 3'-OH of the base sequence. Thus, cleaving the label from the probe unblocks the 3'-OH so as to allow a new hybridisation probe to ligate thereto in the next sequencing cycle.

Theoretically the predetermined length of the base sequence is limited only by considerations of ligase fidelity. The longer the base sequence, the stronger the hybridisation will be between probe base sequence and single-stranded DNA. Thus, a length of 10 or 11 is thought to be about the maximum before ligase fidelity becomes unacceptable. However, practically speaking, sequences of this length would require too many unique labels to be useful, whereas, shorter base sequences require fewer unique labels. Preferably, the predetermined length of the base sequence is from 2 to 6, more preferably 4.

The invention further provides a kit for sequencing DNA, which comprises an array of hybridisation probes, each probe comprising a label cleavably attached to a known base sequence of predetermined length, the array containing all possible base sequences of that predetermined length and the base sequences being incapable of ligation to each other. The array of hybridisation probes is preferably as defined above. The kit may further comprise instructions for use in a method of sequencing DNA. Use of the kit is therefore provided for a method of sequencing DNA, especially the method described above.

The invention will now be described in further detail by way of example only, with reference to the accompanying drawings, in which:

BRIEF DESCRIPTION OF THE DRAWINGS

FIG. 3 shows typical adaptor molecules for use in the invention;

Figure 1A:
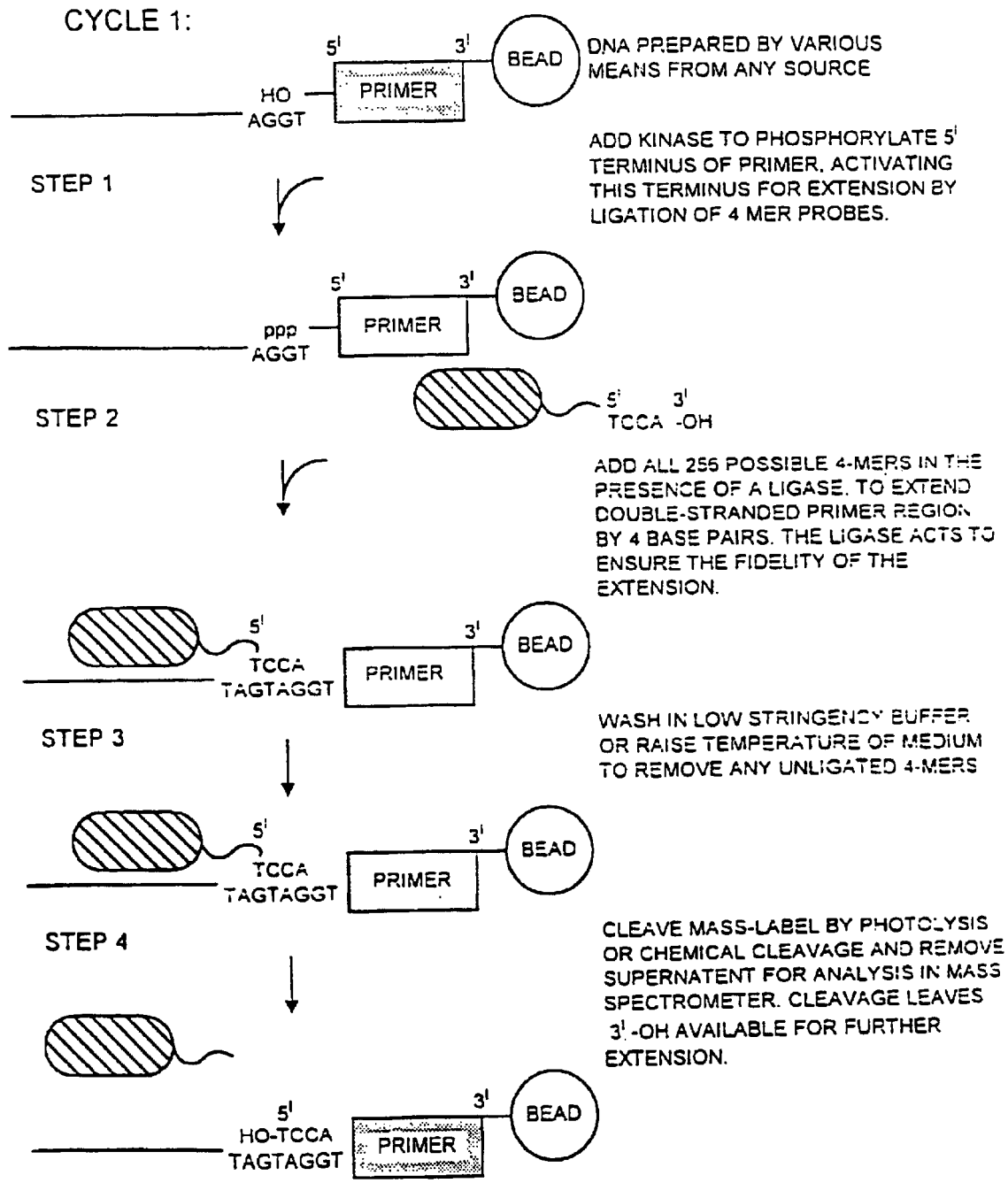
FIGS. 1a and 1b show respectively first and second cycles of a preferred process according to the invention.
Figure 1B:
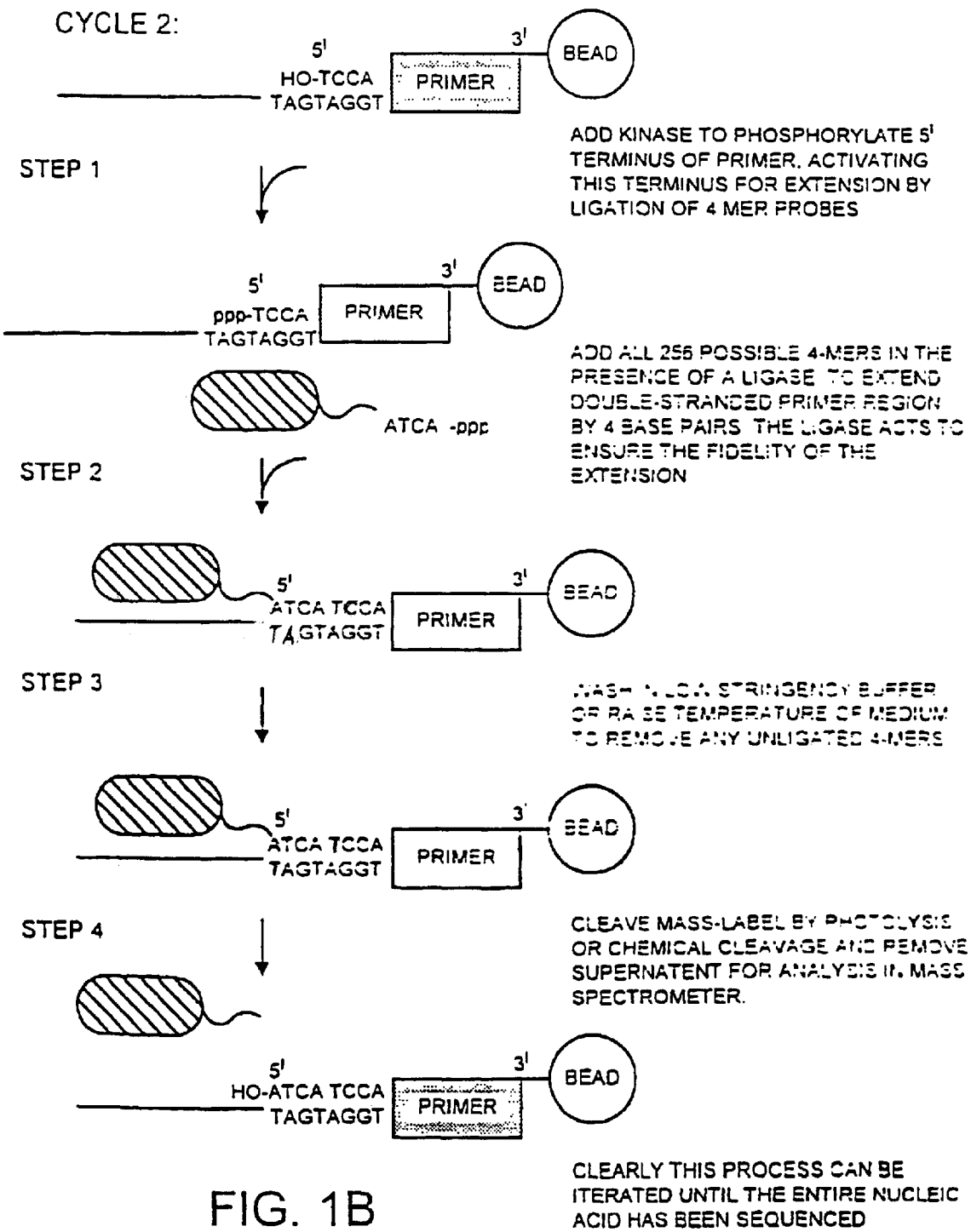

Parallel sequencing of sorted populations of nucleic acids by primer extension sequencing:

This invention is a process that allows a heterogenous population of nucleic acid fragments, generated by various means, to be sequenced simultaneously. The process provides a novel strategy for sequencing genomic DNA that potentially could avoid the need for biological subcloning hosts and vectors.

The sequencing process described here allows one to produce nucleic acid fragment populations in a reproducible manner that can then be sorted into subsets and finally sequenced by an iterative process of ligation of probes to an immobilised single-stranded DNA molecule.

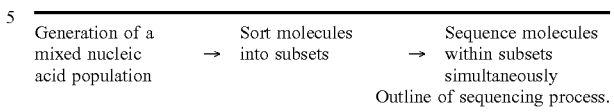

Outline of sequencing process.

The sequencing steps use short single stranded oligonucleotides of a predetermined length to probe the sequence of single-stranded immobilised template nucleic acid fragments. Single-stranded regions adjacent to a primed region are determined by ligating the probe oligonucleotides to the primer and determining their identity on the basis of a tag carried by the oligonucleotides. The label determines the sequence of the oligonucleotide probes. Nucleic acid fragments are probed as heterogenous sets and sequence information is determined by measuring the quantity of label of correctly hybridised and ligated probes.

Sequencing can be performed in either a 5' to 3' format or in a 3' to 5' format. Uncontrolled extension in the 5' to 3' format is prevented by reversibly blocking the 3'-OH at the terminus of the probes prior to addition of the probes to the extending primer. After ligation of probe to primer any unligated probe is washed away. The quantity of ligated probes is determined and the 3' terminus is unblocked to allow the next cycle of probing to be performed on the extended primer. In the 3' to 5' format, uncontrolled extension of the primer is controlled by using a phosphorylation step to add a triphosphate entity onto the extending primer's 5'-OH group. Probes are synthesised without any phosphate groups at the 5' terminus, so after each addition of probes to the extending primer, the 5'-OH must be phosphorylated to permit further extension.

The sequence of individual fragments is determined by comparing quantities of label for each type of probe in each cycle of the sequencing process with quantities derived in previous and subsequent cycles. The invention provides a method for analysing heterogenous sub-populations of nucleic acids without spatially resolving them. This is achieved by a signal acquisition and signal processing procedure that allows sequences to be identified on the basis of their relative quantities.

This process does not require traditional gel methods to acquire sequence information. Since the entire process takes place in solution and is an iterative process, the steps involved could be performed by a liquid-handling robot.

Sequencing Large Nucleic Acid Molecules:

It is not necessary to sequence an entire molecule at once to determine its sequence, which is fortunate as it is a practical impossibility, at the moment, to sequence molecules as large as chromosomes. It is calculated that any given sequence 17 bp long should be unique within the human genome. Similar calculations can be performed for genomes that are of different sizes. This consideration means that large nucleic acids or entire genomes can be sequenced by degradation into short overlapping fragments, >17 bp in length, which can then be sequenced and the total genome sequence can thence be reconstructed using software to determine contig overlaps.

Preparing a Nucleic Acid for Sequencing:

To sequence a complete nucleic acid of significant size is practically very difficult. This process requires fragmentation of the target nucleic acid and sorting into sub-populations that are small enough to allow simultaneous sequencing. Various embodiments of the sorting process have been described previously in the Gene Profiling patent application and the prior sequencing application. Only a minor variation in the use of adaptors to provide distinct termini in a population of generic nucleic acids is discussed here.

Immobilising a Specific Terminus in a Population of Nucleic Acids:

An important factor is immobilisation of nucleic acids at one terminus. This requires that an arbitrarily generated fragment have directionality, i.e. it requires two distinguishable termini. This can be achieved using adaptors. Two types of adaptors are required to identify two distinct termini. Exemplary adaptors are shown in the attached figures. Adaptor 1 provides immobilisation and the recognition site for a type II restriction endonuclease that generates blunt-ended fragments, in this example the enzyme chosen is BsuRI which is methylation sensitive. DNA to be sequenced would be synthesised with 5-methyl cytosine while adaptors would be synthesised with unmethylated cytosine so that only adaptors would be sensitive to cleavage by BsuRI. Adaptor 2 provides a type IIs restriction endonuclease recognition site or alternatively a restriction sight for a second ordinary type II restriction endonuclease.

The adaptors need to be attached to the nucleic acid fragments. Effecting attachment depends on the means used to fragment the population, but assuming random fragmentation with the some form of nuclease that generates known sticky-ends, ligation of forms of both adaptor types bearing complementary sequences will be effective or blunt-ended adaptors could be used as shown in FIG. 3. This generates fragments of three types: fragments with both ends carrying adaptor 1, fragments with both ends carrying adaptor 2 and thirdly fragments carrying adaptor 1 at one end and adaptor 2 at the other. Statistically the third type of fragment will be in the majority. If the immobilisation effector on adaptor 1 is biotin then the fragments carrying adaptor 1 can be immobilised on a solid phase matrix derivitised with avidin. The fragments carrying adaptor 2 at both ends can be washed away. Those fragments carrying two immobilisation adaptors might be immobilised at both termini depending on the fragment lengths. Cleavage with the type IIs restriction endonuclease whose binding site is carried by adaptor 2 will generate ambiguous sticky-ends at one terminus of the fragments bearing both types of adaptor. The fragments bearing two type 1 adaptors will be unchanged. The cleaved adaptor fragments can then be washed away with the type IIs restriction endonuclease. A second cleavage with the ordinary type II restriction endonuclease whose cleavage site is in adaptor 1 will release the remaining immobilised fragments that bore one copy of each adaptor at their termini. Those fragments should have an ambiguous sticky-end at the terminus that bore adaptor two and can thus be sorted as described below. Those fragments that carried two copies of adaptor 1 will have blunt-ended termini and will not bind the array and can thus be washed away. In this way a population of nucleic acid fragments can be specifically immobilised at one terminus with the other terminus prepared for sequencing. As long as multiple copies of each sequence is present then statistically the vast majority of sequences should be represented in the portion of the population carrying both adaptors and thus every sequence should be sequenced at least once. Any gaps should become apparent in the contig reconstruction process and can then be specifically searched for using primers targeted at sequences flanking the gaps.

Alternatively sorting can be left until a later step if adaptor 2 bore a cleavage site for an ordinary type II restriction endonuclease that generated a known sticky-end. Preferably a methylation sensitive restriction enzyme would be required to do this. The resultant fragments can then be immobilised on beads for further processing such as further amplification or in order to render the fragments single-stranded. One skilled in the art could almost certainly think of other methods of acheiving distinct termini. Furthermore, if a restriction map for the target DNA is known then designing adaptors or protocols to distinguish the termini of fragments is simpler.

Figure 4:
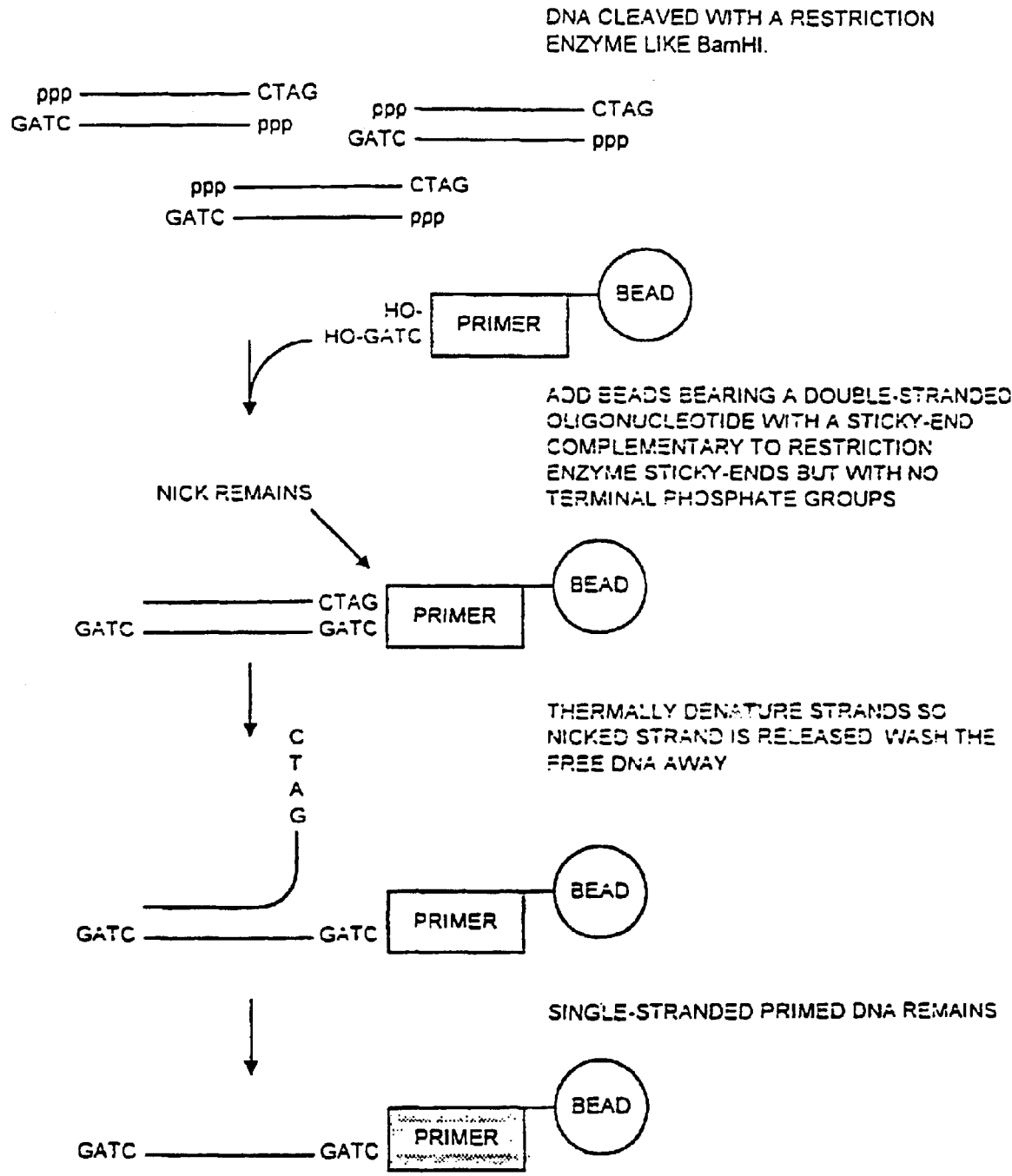
FIG. 4 shows a preferred method of producing target DNA for sequencing in according with the invention.
Figure 5:
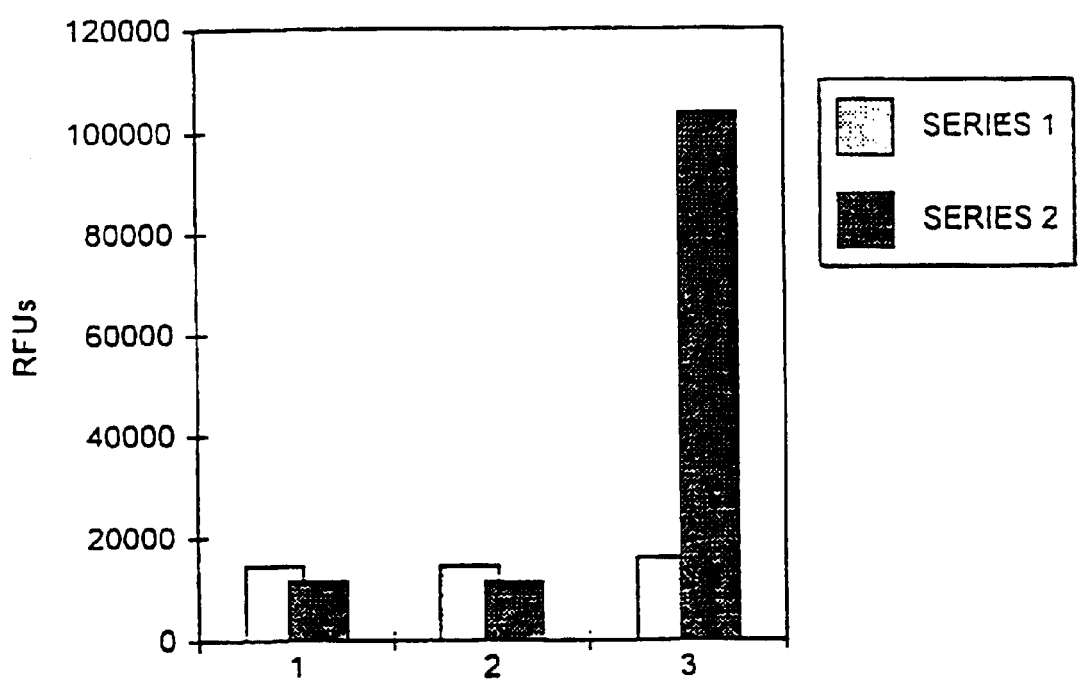
FIG. 5 shows a bar chart depicting the data for the first cycle of a 4-mer sequencing experiment, series I being without ligase and series 2 with ligase.
Figure 6:
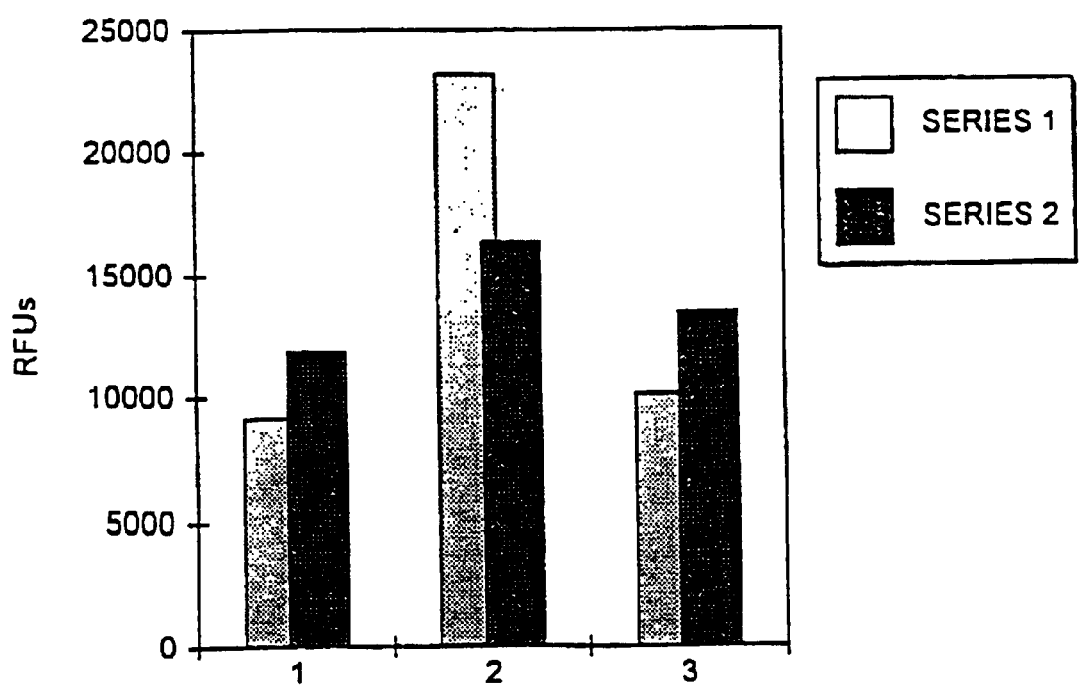
FIG. 6 shows a bar chart depicting the data for the second cycle of the 4-mer sequencing experiment, series I being without ligase and series 2 with ligase.
Figure 7:
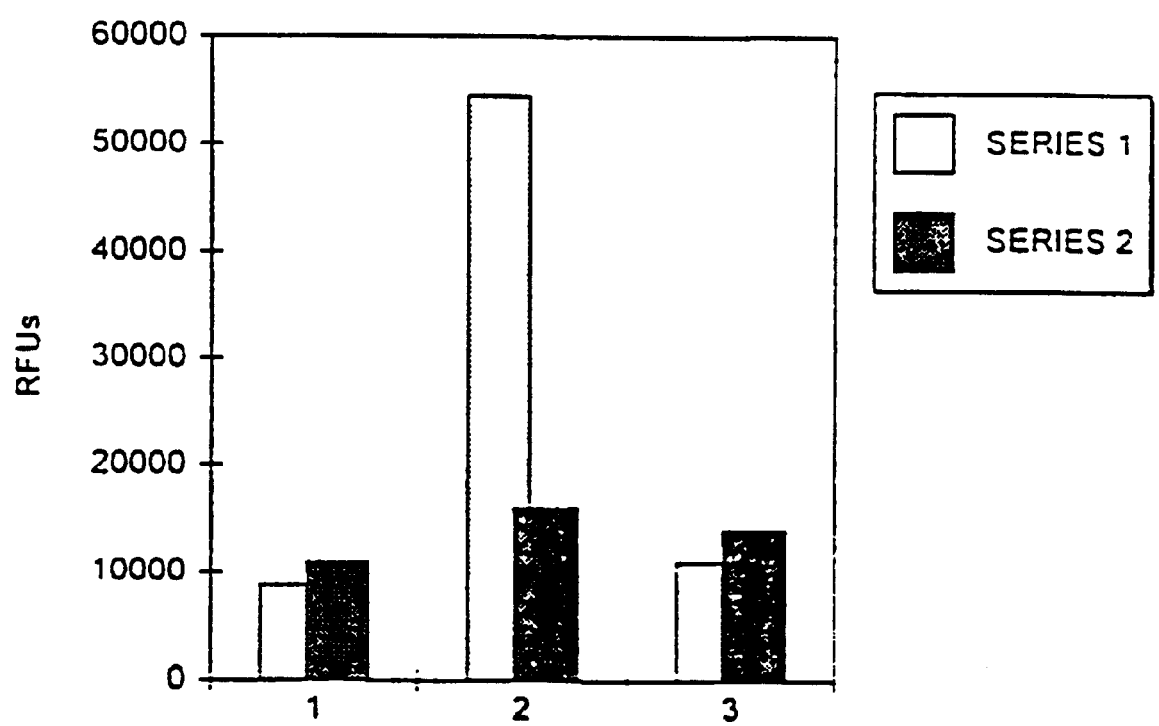
FIG. 7 shows a bar chart depicting the data for the third cycle of the 4-mer sequencing experiment, series I being without ligase and series 2 with ligase.

Generating Single-Stranded DNA for Primer Extension Sequencing:

The sequencing system requires single-stranded DNA fragments to operate on. This is relatively trivial to generate. One need only use beads derivitised with a double-stranded oligonucleotide that has no terminal phosphate groups on its exposed 5' strand. Cleavage of the DNA fragments to be sequenced with an enzyme that leaves 5' phosphates or use of a kinase to generate 5' phosphate groups on these fragments is required so that ligation of these fragments to the beads can take place, see FIG. 4. The ligation will leave the strand linked to the 5' terminus of the immobilised oligonucleotide with a nick. Raising the temperature or otherwise producing denaturing conditions will remove the nicked strand, leaving an immobilised single stranded DNA.

DNA from phage M13 is single-stranded and this is often used as a sequencing vector to generate single-stranded templates for Sanger sequencing.

Sorting Molecules into Subsets:

Once a fragment population has been amplified and distinct termini established for each fragment, as described above the fragments with ambiguous sticky-ends can be sorted. Sorting can be effected in the same way as described in the Gene Profiling application GB 9618544.2 using beads derivitised with oligonucleotides complementary to the possible sticky-ends that might be generated. The sorting process can be repeated with the first sorted populations using adaptors to provide another terminal type IIs restriction endonuclease site. This will allow another set of ambiguous sticky-ends to be generated allowing further sub-sorting until the nucleic acid fragment population is of the correct size for unambiguous sequence determination.

One can effect also sorting with oligoucleotides chips, allowing simultaneous analysis of fragments. This is particularly desirable as the quantities of reagents required would be much smaller than for a series of wells. This sorting method is compatible with fluorescence as a means of detection. A population of DNA fragments with an ambiguous sticky-end at one terminus can be sorted on an oligonucleotide chip by ligation of the exposed sticky-end to its complement. Thus for a 4 bp sticky-end, a chip with the 256 possible 4-mers present at discrete locations on its surface would be required.

This sorting process above generates, for a 4 bp ambiguous sticky-end, 256 sub-populations. This may generate nucleic acid populations small enough to begin sequencing or further sub-sorting may be necessary.

Primer Extension and Parallel Sequencing of Heterogenous Populations of Nucleic Acid Fragments:

Sequencing a Single Molecule by Ligation of Single Stranded Oligenucleotides to a Primer:

This process can be understood first by explaining it for the case of a single nucleic acid. Consider a single nucleic acid, immobilised at one terminus to a fixed insoluble matrix. This molecule is rendered single stranded, except for a short strength of double-stranded DNA at the immobilised terminus of the molecule. This primer sequence could be provided by the adaptor used to immobilise the terminus.

Figure 2A:
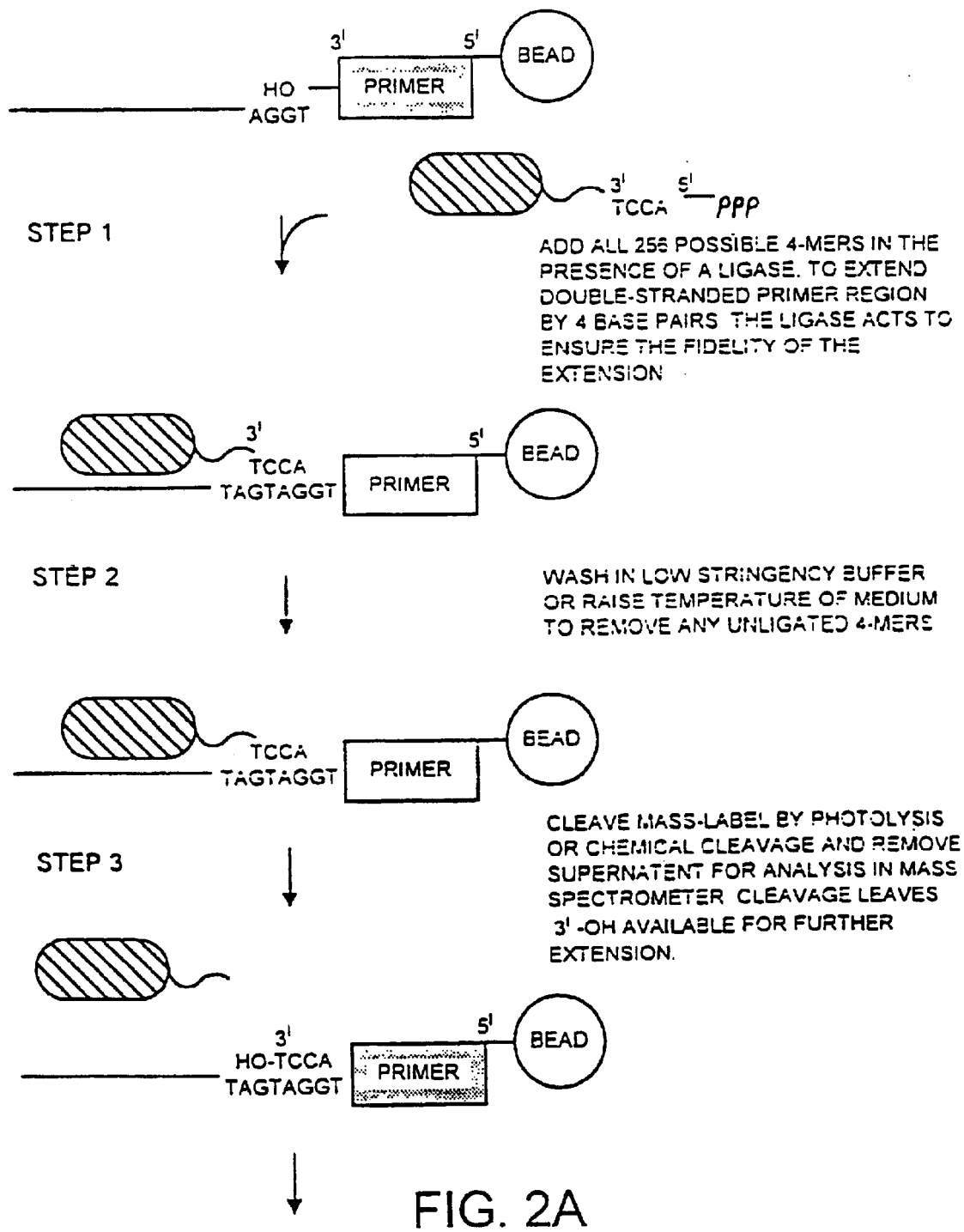
FIGS. 2a and 2b respectively first and second cycles of an alternative process according to the invention.
Figure 2B:
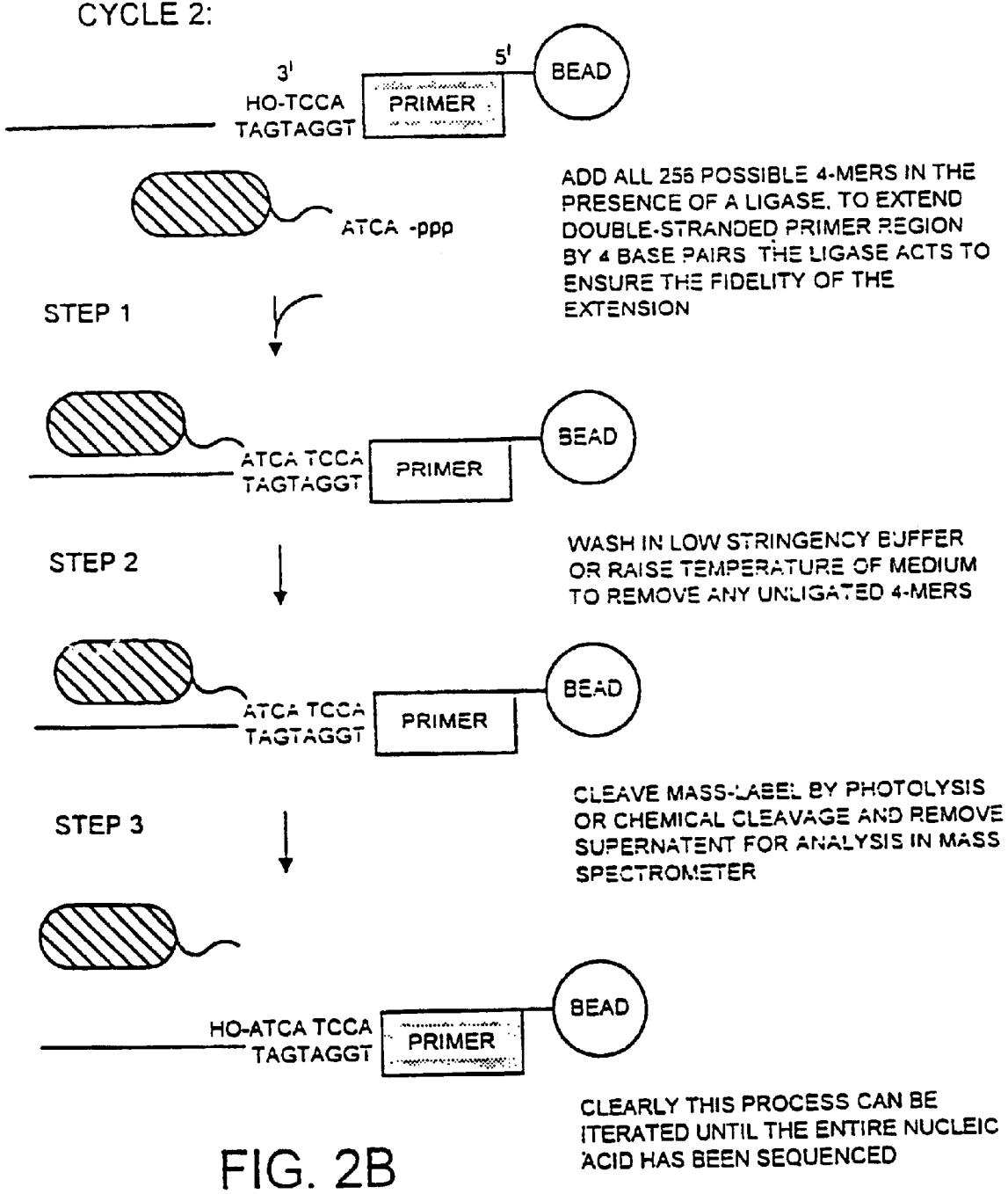

To determine the sequence of this single-stranded molecule one can probe the immobilised nucleic acid with every one of the possible 256 single-stranded 4 base oligonucleotides. Each of these would carry a unique identifying label corresponding to its known, sequence of 4 bp. In the 5' to 3' format (see FIGS. 2a and b), the label could be attached to the 3'-OH effectively blocking them from further extension, or a separate blocking group can be used and the label can be attached elsewhere in the molecule. In the 3' to 5' format (see FIGS. 1a and b ) there is no particular advantage in attaching the mass label to any particlar part of the probe, except that it is less likely to interfere with the ligase if it is added to the terminus of the probe.

If the oligonucleotides are added in the presence of a ligase, the oligonucleotide complementary to the 4 bases of sequence adjacent to the primed double-stranded region, will be ligated to the primer. The immobilised matrix can then be washed to remove any unbound oligonucleotides. To determine the sequence of the 4 base oligonucleotide that ligated to the primer, one need only analyse the label attached to the 3' end of the oligonucleotide. The labelling system for use with this invention is described in a PCT patent application filed concurrently with the present application (Page White & Farrer Ref: 86359). This describes 'mass labelling' in which the mass of the label identifies its carrier. Such labels can be made photolabile or cleavable by a specific agent. Cleavage of the label will release it into solution in which it can be injected into an electrospray mass spectrometer for analysis, which will determine the sequence of the oligonucleotide and furthermore, its quantity.

In the preferred embodiment, a photolysable linker would connect the mass label to the 3'-OH which when cleaved would regenerate the 3'-OH with as high an efficiency as possible. The primer has then been extended by 4 known bases and the cycle can be repeated to determine the next 4 bp of sequence. This process can be repeated iteratively until the entire molecule has been sequenced.

An alternative implementation to using photolysable mass labels at the 3'-OH of each 4-mer oligonucleotide would be to cap the 3'-OH with a phosphate group. The mass-label could be attached to another part of the molecule from which it can be released independently of the uncapping reaction of the 3' terminus. Uncapping of the 3' terminus can be effected by washing the immobilised DNA with alkaline phosphatase which will readily remove the capping phosphate from the 3'-OH leaving it available for the next cycle of the sequencing process.

Conceivably this system could be implemented with other labelling schemes, but most other labelling schemes do not generate sufficient, unique labels to be practical. Using fluorescence the same system could be implemented, but since only 4 good dyes are commercially available, the 4 bp oligonucleotides would have to be tested in 64 groups of 4, rather than all at once. Similar considerations apply to use of radiolabels, but here, each oligo would be added one at a time. Other labels include carbohydrates, biotin amongst others.

Actually mass-labelled oligonucleotides would probably be added in two sets of 128 such that each member in the first set would have its complement in the other set. This overcomes the problem of cross-hybridisation between complementary 4-mers.

Sequencing a Population of Nucleic Acid Fragments:

The same process can be applied to a heterogeneous population of immobilised nucleic acids allowing them to be analysed in parallel. To be successful when applied to a population of nucleic acids, this method relies on the assumption that statistically 1 out of 256 molecules within the total population will carry each of the possible 4 bp sequences adjacent to the double stranded primer region. If one sub-sorts one's nucleic acid population into manageable subsets of less than 256 fragments, one would expect that almost all will have different ambiguous sticky-ends (there is about a 1 in 1000 chance of there being 2 distinct DNAs having the same 4 bp sequence at any given point if 100 distinct sequences are analysed simultaneously) so for most purposes one can assume that a hybridisation signal corresponds to a single DNA type. This all assumes that DNA sequences are random sequences of bases which is not strictly true but is a sufficient assumption for the purposes of this invention. Obviously 1 in a 1000 is not a small probability and sequences will often have the same 4-mer in a sequencing cycle. However this invention includes an algorithm that can resolve to a great extent any possible ambiguities caused by this occurrence.

Reconstructing Sequences of Target Nucleic Acids:

Repetitions of the primer extension cycle will generate a matrix of quantities of label corresponding to each possible probe. Shown below is a possible matrix for all probes of 4 base pairs in length:

| Sequence to which label corresponds | Cycle 1 | Cycle 2 | Cycle 3 | Cycle 4 |
|---|---|---|---|---|
| AAAA | 5 | 24 | 13 | 7 |
| AAAC | 10 | 5 | 9 | 13 |
| AAAG | 13 | 9 | 15 | 17 |
| ... | ... | ... | ... | ... |
| TTTG | 7 | 13 | 17 | 10 |
| TTTT | 17 | 10 | 7 | 14 |

To reconstruct the sequences to which these quantities of label correspond, this invention may incorporate an algorithm for analysing such a data matrix. Such an algorithm and a computer program for employing the algorithm are described in detail in PCT/GB97/02734. The algorithm attempts to identify a sequence on the basis of its frequency, i.e. a sequence present at a given frequency will have every subsequence present at the same frequency. The algorithm searches through each column of the matrix and attempts to resolve label quantities, that may be sums of sequence frequencies into atomic quantities such that the same set of atomic quantities appear in all columns. The algorithm acheives this by comparing label quantities in a given column with those in the previous and the subsequent columns, except in the case of the first and last columns which can only be compared with the following and previous columns respectively. A given atomic quantity that appears in all columns is then assumed to correspond to a unique sequence.

It two sequences have the same n-mer at a particular point in the sequence, these can be resolved by the quantitative nature of this system in that the quantity of a particular n-mer in a particular ligation will be the sum of the quantities of the two sequences that share the n-mer of the same point. These can be largely resolved by comparison of one cycle with previous and subsequent ligation cycles to identify such sums. This is made particularly simple if the sequences that are being analysed have been amplified by PCR such that the sequence in the lowest quantity is present at not less than half the quantity of the sequence with the greatest frequency, that is to say if the frequency range of sequences lies between some quantity N and 2N and hence readily detectable.

There may be occasional ambiguities that only give partial resolution of the sequences. Further resolution can be obtained by performing the same sequencing process for each sample twice. In each case the length of the probe is different, so for the the first sequencing attempt, probes of 4 base pairs would be used and for the second, probes of 5 base pairs would be used. Comparison of the two matrices will allow the sequences to be resolved with far fewer ambiguities.

Implementation of the Invention:

Practical details of implementing the process are described below.

Adaptors, PCR Primers and Oligonucleotides:
Construction of Oligonucleotides, Adaptors, Primers, etc.

Details and reviews on the construction of oligonucleotides are available in numerous up to date texts, which should allow one skilled in the art to construct primers, adaptors and any other oligonucleotides required by the invention:

Gait, M. J. editor, 'Oligonucleotide Synthesis: A Practical Approach', IRL Press, Oxford, 1990
Eckstein, editor, 'Oligonucleotides and Analogues: A Practical Approach', IRL Press, Oxford, 1991
Kricka, editor, 'Nonisotropic DNA Probe Techniques', Academic Press, San Diego, 1992
Haugland, 'Handkbook of Fluorescent Probes and Research Chemicals', Molecular Probes, Inc., Eugene, 1992
Keller and Manack, 'DNA Probes, 2nd Edition', Stockton Press, New York, 1993
Kessler, editor, 'Nonradioactive Labelling and Detection of Biomolecules', Springer-Verlag, Berlin, 1992.

Of particular importance is the chemistry used to cap the 3'-OH of the probe oligonucleotides. Acid labile and base labile groups are well known and discussed in the texts above. Capping with a phosphate group is also possible using the above texts, such a group can then be controllably removed using a phosphatase such as alkaline phosphatase which is readily available.

Conditions for Using Oligonucleotide Constructs:

Details on effects of hybridisation conditions for nucleic acid probes can be found in be found in references below:
Wetmur, Critical Reviews in Biochemistry and Molecular Biology, 26, 227–259, 1991
Sambrook et al., 'Molecular Clong: A Laboratory Manual, 2nd Edition', Cold Spring Harbour Laboratory, New York, 1989
Hames, B. D., Higgins, S. J., 'Nucleic Acid Hybridisation: A Practical Approach', IRL Press, Oxford, 1988

Ligation:

Ligation of oligonucleotides is a critical aspect of the invention that must be considered. Chemical methods of ligation are known:
Ferris et al, Nucleosides and Nucleotides_8, 407–414, 1989
Shabarova et al., Nucleic Acids Research 19, 4247–4251, 1991

Preferably enzymatic ligation would be used as this has much higher fidelity. Preferred ligases would be T4 DNA ligase, T7 DNA ligase, E. coli DNA ligase, Taq ligase, Pfu ligase and Tth ligase. References to the literature are given below:
Lehman, Science 186, 790–797, 1974
Engler et al., 'DNA Ligases', pg 3–30 in Boyer, editor, 'the Enzymes, Vol 153', Academic Press, New York, 1982
Protocols for Use of Ligases can be Found In:
Sambrook et al, cited above
Barany, PCR Methods and Applications, 1: 5–16, 1991
Marsh et al., Strategies 5, 73–76, 1992

Phosphorylation of Nucleic Acids:

When ligases and restriction endonucleases are used, there are changes made to the 5' phosphates of nucleic acid backbone sugar molecules. It is critical to this invention that extension of primers by ligated oligonucleotides be tightly controlled such that only one oligonucleotide is ligated to each extending primer in each cycle of the sequencing process. It is also possible to alter the phosphorylation state of oligonucleotides, adaptors or target nucleic acids during their synthesis or later, in versions of the process. Included are references to literature regarding use of phosphatases, kinases and chemical methods:
Horn and Urdea, Tetrahedron Lett. 27, 4705, 1986
Sambrook et al, cited above The 5'-hydroxy gp of the oligonucleotides can be chemically phosd. by means of phosphoryl chloride (POCl$_3$).

Restriction Endonuclesaes:

Numerous type II and IIs restriction endonucleases exist and could be used with this invention. Table 1 below gives a list of examples but is by no means comprehensive. A literary review of restriction endonucleases can be found in Roberts, R., J. Nucl. Acids Res. 18, 2351–2365, 1988. New enzymes are discovered at an increasing rate and more up to date listings are recorded in specialist databases such as REBase which is readily accessible on the internet using software packages such as Netscape or Mosaic and is found at the World Wide Web address: http://www.neb.com/rebase/. REBase lists all restriction enzymes as they are discovered and is updated regularly, moreover it lists recognition sequences, isoschizomers of each enzyme, manufacturers and suppliers and references to them in scientific literature. The protocol would be much the same irrespective of the type IIs restriction endonuclease used but the spacing of recognition sites for a given enzyme within an adaptor would be tailored according to requirements and the enzymes cutting behaviour. (see figure n above)

TABLE 1

A sample of type IIs restriction endonucleases

| Enzyme Name | Recognition sequence | Cutting site |
|---|---|---|
| Fok1 | GGATG | 9/13 |
| BstFs1 | GGATG | 2/0 |
| SfaNI | GCATC | 5/9 |
| HgaI | GACGC | 5/10 |
| BbvI | GCAGC | 8/12 |

The requirement of the process is the generation of ambiguous sticky-ends at the termini of the nucleic acids being analysed. This could also be achieved by controlled use of 5' to 3' exonucleases. Clearly any method that achieves the creation of such sticky-ends will suffice for the process.

Similarly ordinary type II restriction endonucleases required by this invention can be found in the reference sources listed above. Details on methylation sensitivity and other means of controlling enzyme action can be found in the references given in REBase or can be acquired from the manufacturers.

Solid Phase Supports:

A full discussion of solid phase supports can be found in Brenner PCT/US95/12678 pg 12–14. This is an important issue in the use of fluorimetry to determine sequence abundance in that the design of supports will affect the acquisition of fluorescent signals which must be maximised for this process to be effective.

Mass Spectrometry of Labels on Oligonucleotides:

Electrospary mass spectrometer is the preferred technique for identification of labels attached to oligonucleotides since it is a very soft technique and can be directly coupled to the liquid phase molecular biology used in this invention. For a full discussion of mass spectrometry techniques see:

R. A. W. Johnstone and M. E. Rose, "Mass Spectrometry for chemists and biochemists" 2nd edition, Cambridge University Press, 1996.

Mass Labels:

For any practically or commercially useful system it is important that construction of labels be as simple as possible using as few reagents and processing steps as possible. A combinatorial approach in a which a series of monomeric molecular units are available to be used in multiple combinations with each other Amino Acids:

With a small number of amino acids such as glycine, alanine and leucine, a large number of small peptides with different masses can be generated using standard peptide synthesis techniques well known in the art. With more amino acids many more labels can be synthesised.

E. Atherton and R. C. Sheppard, editors, 'Solid Phase Peptide Synthesis: A Practical Approach', IRL Press, Oxford.

Carbohydrates:

Similarly carbohydrate molecules are useful monomeric units that can be synthesised into heteropolymers of differing masses but these are not especially amenable to ESMS.

Gait, M. J. editor, 'Oligonucleotide Synthesis: A Practical Approach', IRL Press, Oxford, 1990

Eckstein, editor, 'Oligonucleotides and Analogues: A Practical Approach', IRL Press, Oxford, 1991

Other Labelling Chemistries:

Clearly almost any molecule can be tacked onto another as a label. Obviously the properties of such labels in the mass-spectrometer will vary. In terms of analysing biomolecules it will be important that the labels be inert, etc., as discussed previously. Cholesterol groups and glyceryl groups are possibilities that could be used but these are intrinsically relatively large molecules and the scope.

Designing Nolecules with Favorable Mass-Spectrometry Purposes:

One can synthesis labels using standard organic chemistry techniques. Such labels ought to carry amine derivatives, quaternary ammonium ions or positive sulphur centres if positive ions are sought. These have extremely good detection properties that generate clean sharp signals. Similarly, negatively charged ions can be used, so molecules with carboxylate moieties can be used. Labels for MALDI mass spectrometry can be generated by derivitising known molecules that are excitable by UV laser light, such as sinapinnic acid or cinnamic acid, of which a number of derivatives are already commercially available. For a text on organic chemistry see:

Vogel's "Textbook of Organic Chemistry" 4th Edition, Revised by B. S. Furniss, A. J. Hannaford, V. Rogers, R. W. G. Smith & A. R. Tatchell, Longman, 1978.

Linkers:

An important feature of this invention is attachment of labels to their relevant biomolecules and in the 5' to 3' sequencing embodiment, the need for removable blocking groups is also critical. For details on these issues see:

Theordora W. Greene, "Protective Groups in Organic Synthesis", 1981, Wiley-Interscience Fluorimetry:

Certain embodiments of the process could use oligonucleotides bearing fluorescent labels. Detection of fluorescent signals can be performed using optical equipment that is readily available. Fluorescent labels usually have optimum frequencies for excitation and then fluoresce at specific wavelengths in returning from an excited state to a ground state. Excitation can be performed with lasers at specific frequencies and fluorescence detected using collections lenses, beam splitters and signal distribution optics. These direct fluorescent signals to photomultiplier systems which convert optical signals to electronic signals which can be interpreted using appropriate electronics systems.

Breener PCT/US95/12678 pg 26–28 gives a full discussion.

Liquid Handling Robotics:

For this process to be practically useful, automation is essential and liquid handling robots can be acquired from various sources such as Applied Biosystems.

Example-Sequencing by the Ligation of 4-mers

An experiment was carried out involving the extension of a sequencing primer, hybridised to a single stranded DNA template, by the stepwise ligation of 4mers. In general the 4mers will contain labels with which the sequence of the 4mer and hence the template can be derived. 256 4mers are required to cover all possible variations. Each 4mer must contain a blocking group, preferably the identifying label, at the 3'hydroxy to ensure that only one 4mer is ligated to the sequencing primer with each cycle. After successful ligation the blocking group (and the label if different) is removed by chemical or other means to expose the 3'hydroxyl of the 4mer. The label, and hence the sequence, is then identified. The 4mer is then available for the ligation of the next 4mer in the second cycle.

In order to demonstrate the effectiveness of removing of the 3'blocking group of the ligated 4mer a non-blocked 4mer was ligated to the sequencing primer in a separate reaction and this was then used as a template for the next cycle. The Experiment is depicted in schematic form below:

Sequencing template—captured to streptavidin coated plate via a biotin molecule (B):

5'CTGGTACGTACATACGACTA'3OH
3'GACCATGCATGTATGCTGATACAGATGAATGTATT
TGATAGTCCTAGCTAAAG4'B

Cycle 1

5'CTGGTACGTACATACGACTA'3OH
3'GACCATGCATGTATGCTGATACAGATGAATGTATTTGATAGTCCTAGCTAAAG5'B
+
5'PO4-TGTC-3'FAM, 5'PO4-TACT-3'FAM, 5'PO4-TAAA-3'FAM
=

-continued

Cycle 1

5'CTGGTACGTACATACGACTA-TGTC-FAM
3'GACCATGCATGTATGCTGAT-ACAGATGAATGTATTTGATAGTCCTAGCTAAAG5'B

Only 5'PO4-TGTC-3'FAM ligates to give a signal which identifies the first 4 bases ('3ACAG'5) of the template. To simulate the deprotection of the above species the following reaction was carried out:

5'CTGGTACGTACATACGACTA'3OH
3'GACCATGCATGTATGCTGATACAGATGAATGTATTTGAT(N)14-5'B
+
5'PO4-TGTC-3'OH
=
5'CTGGTACGTACATACGACTA-TGTC-3'OH
3'GACCATGCATGTATGCTGAT-ACAGATGAATGTATTTGAT(N)14-5'B

The above species was then used as a template for Cycle 2.

Cycle 2

5'CTGGTACGTACATACGACTA-TGTC-3'OH
3'GACCATGCATGTATGCTGAT-ACAGATGAATGTATTTGAT(N)14-5'B
+
5'PO4-TGTC-3'FAM, 5'PO4-TACT-3'FAM, 5'PO4-TAAA-3'FAM
=
5'CTGGTACGTACATACGACTA-TGTC-TACT-FAM
3'GACCATGCATGTATGCTGAT-ACAG-ATGAATGTATTTGAT(N)14-5'B

Only 5'PO4-TACT-3'FAM ligates to give a signal which identifies the next 4 bases (3ATGA'5) of the template.
Also to simulate the deprotection of the above species the following reaction was carried out:

5'CTGGTACGTACATACGACTA-TGTC-3'OH
3'GACCATGCATGTATGCTGAT-ACAGATGAATGTATTTGAT(N)14-5'B
+
5'PO4-TACT-3'OH,
=
5'CTGGTACGTACATACGACTA-TGTC-TACT-OH
3'GACCATGCATGTATGCTGAT-ACAG-ATGAATGTATTTGAT(N)14-5'B

The above species was then used as a template for Cycle 3.

Cycle 3

5'CTGGTACGTACATACGACTA-TGTC-TACT-OH
3'GACCATGCATGTATGCTGAT-ACAG-ATGAATGTATTTGAT(N)14-5'B
+
5'PO4-TGTC-3'FAM, 5'PO4-TACA-3'FAM, 5'PO4-TAAA-3'FAM
=

-continued

Cycle 3

5'CTGGTACGTACATACGACTA-TGTC-TACT-TACA-FAM
3'GACCATGCATGTATGCTGAT-ACAG-ATGA-ATGTATTTGAT(N)14-5'B

Only 5'PO4-TACA-3'FAM ligates to give a signal which identifies the next 4 bases (3ATGT'5) of the template.
Therefore, through 3 cycles of ligation of 4mers the sequence ACAGATGAATGT of the template was deduced.

Materials:
Oligonucleotides:
  sequencing primer
  5'CTGGTACGTACATACGACTA'3OH
  sequencing template (contains a 5' biotin molecule)
  3'GACCATGCATGTATGCTGATACAGATGAATGTATT
  TGATAGTCCTAGCTAAAG4'B
  4mers used
  5'PO4-TGTC-3'FAM, 5'PO4-TACT-3'FAM, 5'PO4-TAGA-FAM, 5'PO4-TACA-FAM, 5'PO4-TGTC-3'OH, 5'PO4-TACT3'OH
  All oligos were synthesised by Oswel DNA (UK).
Solutions:

| | |
|---|---|
| wash solution | 50 mM Tris-HCl pH7.6 |
| | 10 mM MgCl$_2$ |
| binding solution | 50 mM Tris-HCl pH7.6 |
| | 10 mM MgCl$_2$ |
| | 1 M NaCl |
| ligase buffer | 50 mM Tris-HCl pH7.6 |
| | 10 mM MgCl$_2$ |
| | 10 mM DTT |
| | 1 mM ATP |
| | 50 ug/ml BSA |

Methods:
Hybridisation of the Sequencing Primer to the Template
Aliquots with 500 ul of 0.5 times binding solution containing 5 pmol/ul of each of the sequencing primer and template were heated at 95° C. for 5 mins and then allowed to cool to room temperature over 2 hours. They were then incubated at 4° C. for 1 hour and frozen at −20° C. until used.
This will now be referred to as 'the sequencing template'.
Capture of the Sequencing Template
20 pmol (4 ul)+21 ul of binding solution was added to each well of a black streptavidin coated 96 well microtitre late (Boehringer Mannheim) and incubated at room temperature for 1 hour. The wells were then washed twice with 200 ul of wash solution and once with 50 ul of ligase buffer. The plates were then stored at 4° C. until used.
Cycle 1
Three groups of reactions, one group with a specific 4mer (TGTC) and two with non-specific 4mer (TACT and TAAA) were set up as follows.
Four reactions were set up containing 5% PEG, 400 units of ligase (New England Biolabs) and 100 pmol of 4mer in 25 ul of ligase buffer for the following 4mers: 5'PO4-TGTC3'-FAM, 5'-PO4-TACT3'-FAM and 5'PO4-TAAA3'FAM. Also four reactions for the same 4mers were set up in the same way, but without the inclusion of the ligase to control for non-specific binding of the 4mers.

To simulate a deprotected, successfully ligated 4mer to the sequencing template 48 reactions containing 5% PEG, 400 units of ligase (New England Biolabs) and 100 pmol of 5'PO4-TTC3'OH in 25 ul of ligase buffer were set up.

The above reactions were then added to wells of the microtitre plate containing the sequencing template and incubated at 4° C. for 30 minutes followed by 16° C. for 1 hour. The wells were then washed 3 times with 100 ul of wash solution. 100 ul of wash solution was added to each well. The amount of 4mer ligated to the sequencing template was assessed by measuring the Florescence of any FAM molecule present using a Biolumin 960 fluorescent microtitre plate reader (Molecular Dynamics) using the Xperiment 1.1.0 software (Molecular Dynamics).

Data for Cycle 1

The following data for Cycle 1 are expressed as relative fluorescent units (RFUs) obtained from the reactions which contained ligase:

|      | TAAA-FAM | TACT-FAM | TGTC-FAM |
|------|----------|----------|----------|
|      | 10764    | 10878    | 120119   |
|      | 9815     | 9994     | 97638    |
|      | 11635    | 12543    | 98891    |
|      | 12031    | 11188    | 95931    |
| mean | 11069    | 11151    | 103145   |

The following data from Cycle 1 are expressed as relative fluorescent units (RFUs) obtained from the reactions which did not contain ligase:

|      | TAAA-FAM | TACT-FAM | TGTC-FAM |
|------|----------|----------|----------|
|      | 14605    | 13987    | 15134    |
|      | 13638    | 13692    | 15370    |
|      | 13938    | 14823    | 16019    |
|      | 13826    | 13117    | 17849    |
| mean | 14002    | 13905    | 16093    |

These data clearly show that TGTC-FAM has been specifically ligated to the sequencing template. The other 4mers, in the presence of ligase, gave signals similar to those obtained from non-specific hybridisation control reactions.

Therefore, this specific signal provides the first 4 bases (3'ACAG5') of the sequencing template.

Cycle 2

The following reactions were applied to the sequencing template to which the specific 5'PO4-TGTC-3'OH 4mer had been ligated (as described in Cycle 1) to mimic a 4mer which had been deprotected/identified.

Three groups of reactions, one group with a specific 4mer (TACT) and two with non-specific 4mers (TGTC and TAAA) were set up as follows.

Four reactions were set up containing 5% PEG, 400 units of ligase (New England Biolabs) and 100 pmol of 4mer in 25 ul of ligase buffer for the following 4mers: 5'PO4-TGTC3'-FAM, 5'PO4-FACT3'-FAM and 5'PO4-TAAA3'FAM. Also four reactions for the same 4mers were set up in the same way but without the inclusion of the ligase to control for non-specific binding of the 4mers.

To simulate a deprotected, successfully ligated 4mer to the sequencing template 24 reactions containing 5% PEG, 400 units of ligase (New England Biolabs) and 100 pmol of 5'PO4-TACT3'OH in 25 ul of ligase buffer were set up.

The above reactions were then added to wells of the microtitre plate containing the sequencing template, with 5'PO4-TGTC-3'OH ligated to it as described in cycle 1, and incubated at 4° C. for 30 minutes followed by 16° C. for 1 hour. The wells were then washed 3 times with 100 ul of wash solution. 100 ul of wash solution was added to each well the amount of 4mer ligated to the sequencing template was assessed by measuring the Florescence of any FAM molecule present using a Biolumin 960 fluorescent microtitre plate reader (Molecular Dynamics) using the Xperiment 1.1.0 software (Molecular Dynamics).

Data for Cycle 2

The following data for Cycle 2 are expressed as relative fluorescent units (RFUs) obtained from the reactions which contained ligase:

|      | TAAA-FAM | TACT-FAM | TGTC-FAM |
|------|----------|----------|----------|
|      | 9238     | 24071    | 9693     |
|      | 8207     | 24455    | 9415     |
|      | 10312    | 22294    | 11071    |
|      | 9153     | 21641    | 10815    |
| mean | 9227     | 23340    | 10248    |

The following data from Cycle 2 are expressed as relative fluorescent units (RFUs) obtained from the reactions which did not contain ligase:

|      | TAAA-FAM | TACT-FAM | TGTC-FAM |
|------|----------|----------|----------|
|      | 12532    | 16025    | 13917    |
|      | 11947    | 15651    | 13573    |
|      | 12040    | 17587    | 13049    |
|      | 11908    | 16464    | 12998    |
| mean | 12107    | 16432    | 13384    |

As with Cycle 1, Cycle 2 produces a clear signal from the specific 4mer ligation as compared to the non-specific 4mer ligations and the non-specific hybridisation control reactions which lacked ligase.

Therefore cycle 2 has produced the next 4 bases (3'ATGA5') of the sequencing template.

Cycle 3

The following reactions were applied the sequencing template to which the specific 5'PO4-TACT-3'OH 4mer had been ligated (as described in Cycle 2) to mimic a 4mer which had been deprotected/identified.

Three groups of reactions, one group with a specific 4mer (TACA) and two with non-specific 4mers (TGTC and TAAA) were set up as follows.

Four reactions were set up containing 5% PEC, 400 units of ligase (New England Biolabs) and 100 pmol of 4mer in 25 ul of ligase buffer for the following 4mers: 5'PO4-TGTC3'-FAM, 5'PO4-TACT3'-FAM and 5'PO4-TAAA3'FAM. Also four reactions for the same 4mers were set up in the same way, but without the inclusion of the ligase to control for non-specific binding of the 4mers.

The above reactions were then added to wells of the microtitre plate containing the sequencing template, with 5'PO4-TACT-3'OH ligated to it as described in cycle 2, and incubated at 4° C. for 30 minutes followed by 16° C. for 1 hour. The wells were then washed 3 times with 100 ul of wash solution. 100 ul of wash solution was added to each well the amount of 4mer ligated to the sequencing template was assessed by measuring the Florescence of any FAM molecule present using a Biolumin 960 fluorescent microtitre plate reader (Molecular Dynamics) using the Xperiment 1.1.0 software (Molecular Dynamics).

Data for Cycle 3

The following data for Cycle 3 are expressed as relative fluorescent units (RFUs) obtained from the reactions which contained ligase:

|      | TAAA-FAM | TACA-FAM | TGTC-FAM |
|------|----------|----------|----------|
|      | 8294     | 61002    | 10307    |
|      | 8136     | 52253    | 9659     |
|      | 10323    | 53848    | 11894    |
|      | 9424     | 51570    | 12443    |
| mean | 9044     | 54668    | 11076    |

The following data from Cycle 2 are expressed as relative fluorescent units (RFUs) obtained from the reactions which did not contain ligase:

|      | TAAA-FAM | TACA-FAM | TGTC-FAM |
|------|----------|----------|----------|
|      | 11605    | 16641    | 14000    |
|      | 11417    | 15414    | 14704    |
|      | 11995    | 17719    | 14443    |
|      | 11959    | 16021    | 14381    |
| mean | 11744    | 16449    | 14382    |

As with Cycles 1 and 2, Cycle 3 produces a clear signal from the specific 4mer ligation as compared to the non-specific 4mer ligations and the non-specific hybridisation control reactions which lacked ligase.

Therefore cycle 3 produced the next 4 bases (3'ATGT5') of the sequencing template.

A total of 12 base (3'ACAGATGAATGT5') were successfully sequenced by three rounds of ligations using a fluorescent system which does not require the use of gel electrophoresis.

The specific 4mers (e.g. TACA in Cycle 3) generally give a slightly higher reading in the non-specific hybridisation reactions, without ligase, compared to the non-specific 4mers. This is due to the fact that they are hybridising to their specific target on the sequencing template and are not being fully removed in the washing steps. These slightly higher signals could be reduced to the levels of the non-specific 4mers by increasing the stringency of the washing steps by lowering the ionic strength or increasing the temperature of the wash solution.

The signals obtained for the reactions with ligase of the mis-matched 4mers are lower than those obtained from the non-specific hybridisation control reactions. This is probably due to the presence of a substance in the ligase solution, which is not being removed by the washing steps, quenching some of the fluorescence. This difference could be removed by improving the washing steps or by including inactivated ligase solution into these reactions thereby insuring the same amount of quenching in all reactions.

To ensure that the maximum possible number of cycles may be carried out using this method, it is important to ensure that the ligation efficiency is very high for each step, so that sufficient template is produced for the next cycle.

What is claimed is:

1. A method for sequencing a heterogeneous population of single stranded DNA molecules simultaneously and without spatial separation, wherein each DNA molecule is present in a unique amount and each DNA molecule bears a primer that provides a double stranded portion, which method comprises the following steps:

a) contacting the plurality of single stranded DNA molecules with hybridization probes, each probe comprising a label cleavably attached to a known base sequence of predetermined length, the array containing all possible base sequences being incapable of ligation to each other, wherein the contacting is carried out in the presence of ligase under conditions to ligate the double stranded portion of each DNA molecule, the probe bearing the base sequence complementary to the single stranded DNA molecule adjacent to the double stranded portion thereby to form an extended double stranded portion which is incapable of ligation to further probes; and b) removing all unligated probes; followed by the steps of:

c) cleaving the ligated probes to release each label;

d) recording the quantity of each label; and e) activating the extended double stranded portion to enable ligation thereto; wherein f) steps (a) to (e) are repeated in a cycle for a sufficient number of times to determine the sequence of each single stranded DNA molecule by determined the sequence of release of each label;

wherein the sequence of each DNA molecule is identified on the basis of the relative quantities of each mass label recorded in sted (d) and the unique amount of each DNA molecule.

2. A method according to claim 1, wherein the array comprises a plurality of sub-arrays which together contain all the possible base sequences, and wherein each sub-array is contacted with the DNA population according to step (b), unligated probes are removed according to step (c), and these steps are repeated in a cycle before step (d) so that all of the subarrays contact the DNA population.

3. A method according to claim 1, wherein the heterogenous population of single stranded DNA molecules is obtained by sorting an initial DNA sample into subpopulations and selecting one of the subpopulations as the target DNA population.

4. A method according to claim 3, wherein the initial DNA sample is cut into fragments, each having a sticky end of known length and unknown sequence, which fragments are sorted into sub-populations according to their sticky end sequence.

5. A method according to claim 1, wherein each single-stranded DNA is immobilized at one end.

6. A method according to claim 1, wherein the known base sequence is blocked at its 3'OH.

7. A method according to claim 6, wherein the step (d) of cleaving the ligated probes to release each label unblocks the 3'-OH of the extended double-stranded portion according to step (f).

8. A method according to claim 7, wherein the label of each probe is cleavably attached to the 3'-OH of the base sequence.

9. A method according to claim 1, wherein the base sequence of each probe is unphosphorylated at both 3' and 5' ends and step (f) comprises phosphorylating the 5'-OH of the extended double-stranded portion.

10. A method according to claim 1, wherein the predetermined length of the base sequence is from 2 to 6.

11. A method according to claim 1, wherein the predetermined length of the base sequence is 4.

* * * * *